(12) United States Patent
Cabri et al.

(10) Patent No.: US 9,133,197 B2
(45) Date of Patent: Sep. 15, 2015

(54) OXIDATED DERIVATIVES OF TRIAZOLYLPURINES USEFUL AS LIGANDS OF THE ADENOSINE A2A RECEPTOR AND THEIR USE AS MEDICAMENTS

(75) Inventors: Walter Cabri, Rozzano (IT); Patrizia Minetti, Rome (IT); Giovanni Piersanti, Urbino (IT); Giorgio Tarzia, Petriano (IT)

(73) Assignee: SIGMA-TAU INDUSTRIE FARMACEUTICHE RIUNITE S.P.A., Rome (IT)

( * ) Notice: Subject to any disclaimer, the term of this patent is extended or adjusted under 35 U.S.C. 154(b) by 725 days.

(21) Appl. No.: 13/257,750

(22) PCT Filed: Mar. 18, 2010

(86) PCT No.: PCT/EP2010/053554
§ 371 (c)(1),
(2), (4) Date: Nov. 14, 2011

(87) PCT Pub. No.: WO2010/106145
PCT Pub. Date: Sep. 23, 2010

(65) Prior Publication Data
US 2012/0053191 A1 Mar. 1, 2012

(30) Foreign Application Priority Data
Mar. 20, 2009 (EP) .................... 09155690

(51) Int. Cl.
*C07D 473/34* (2006.01)
(52) U.S. Cl.
CPC .................... *C07D 473/34* (2013.01)
(58) Field of Classification Search
CPC .................................................. C07D 473/34
USPC ........................................ 544/277; 514/263.2
See application file for complete search history.

(56) References Cited

U.S. PATENT DOCUMENTS 7,230,102 B2 *  6/2007  Giorgio et al. ................ 544/277

FOREIGN PATENT DOCUMENTS

EP          1 054 012        11/2000
WO       WO 03/011864       2/2003

OTHER PUBLICATIONS

Wermuth, Camille. "Molecular Variations Based on Isoteric Replacements." The Practice of Medicinal Chemistry. Academic Press, 1996. pp. 203-237.*
Baraldi, Pier. Chem. Rev. 2008, 108, 238-263.*
Blum, David. Lancet Neurology 2003; 2: 366-74.*
Pedata, Felicita. Anals New York Academy of Sciences. 939 (1). (2006) 74-84.*
Health Communities.com. Movement Disorders, 2014, < http://www.healthcommunities.com/movement-disorders/overview-of-movement-disorders.shtml>.*
Minetti, et al., 2-n-Butyl-9-menthyl-8-[1,2,3]triazol-2-yl-9H-purin-6-ylamine and Analogues as A Adenosine Receptor Antagonists. Design, Synthesis, and Pharmacological Characterization, J. Med. Chemistry (2005) vol. 48, No. 22, p. 6887-6896.

* cited by examiner

*Primary Examiner* — Golam M M Shameem
*Assistant Examiner* — Laura Daniel
(74) *Attorney, Agent, or Firm* — Vedder Price P.C.; Thomas J. Kowalski; Deborah L. Lu (57) ABSTRACT

The present invention relates to new triazolyl purine derivatives of formula (I), processes for their preparation, and to pharmaceutical compositions containing them for the treatment of neurological disorders or cerebral ischaemia for which inhibition of adenosine A2A receptor will result at improving the health state of a patient.

2 Claims, 4 Drawing Sheets

Figure 1: ST3932 efficacy at antagonizing the haloperidol-induced catalepsy in mice

Figure 2: ST4206 efficacy at antagonizing the haloperidol-induced catalepsy in mice

Figure 3: ST3829 efficacy in an anti-parkinsonian animal model

Figure 4: ST3932 efficacy in an anti-parkinsonian animal model

Figure 5: ST4206 efficacy in an anti-parkinsonian animal model

OXIDATED DERIVATIVES OF TRIAZOLYLPURINES USEFUL AS LIGANDS OF THE ADENOSINE A2A RECEPTOR AND THEIR USE AS MEDICAMENTS

FIELD OF THE INVENTION

The present invention relates to new triazolyl purine derivatives, processes for their preparation, and to pharmaceutical compositions containing them for the treatment of neurological disorders for which inhibition of adenosine $A_{2A}$ receptor will result at improving the health state of a patient.

BACKGROUND OF THE INVENTION

Adenosine $A_2$ is an endogenous modulator, which among other effects mediates a general depression of the central nervous system, vasodilatation and inhibition of platelet aggregation.

Adenosine receptors represent a subclass (P1) of the group of purine nucleotide and nucleoside receptors known as purinoreceptors. Up to now, four subtypes of adenosine receptors are known (i.e., $A_1$, $A_{2A}$, $A_{2B}$ (of high and low affinity) and $A_3$ receptors). Adenosine receptors are all coupled to G-proteins; $A_1$ and $A_3$ subtypes are associated with inhibitory G-proteins and the $A_{2A}$ and $A_{2B}$ subtypes are associated with stimulatory G-proteins. Activation of the $A_1$ and $A_3$ receptors causes inhibition of adenylate cyclase and phospholipase C, which inhibits neurotransmission. The $A_1$ receptors are highly expressed in the brain, especially in the hippocampus, thalamus, cerebellum and cortex compared to the $A_3$ receptors which are moderately expressed in the brain. Activation of the $A_{2A}$ and $A_{2B}$ receptors causes activation of adenylate cyclase and phospholipase C, resulting in the stimulation of neurotransmission. $A_{2A}$ receptors are co-expressed in the brain with dopamine D2 receptors, especially in the striatum, olfactory tubercle and nucleus accumbens and are involved in neurodegenerative pathologies.

$A_{2a}$ receptors are densely distributed in the central nervous system (striatum, nucleus accumbens and olfactory tubercles) where they play an important role in the regulation of mood and motor activity (Poulsen, S. A., et al., *Bioorg. Med. Chem.*, 1998, 6, 619; Ongini, E., et al., *Trends Pharmacol. Sci.*, 1996, 17, 364). Parkinson's disease has been treated for more than thirty years by dopamine replacement strategies (Cotzias, G. C., et al., *N. Engl. J. Med.*, 1969, 280, 337). However, because long-term use of dopamine-replacing agents is associated with severely disabling side effects, most notably dyskinesia (Chase T. N., *Neurology*, 1998, 50, S17-S25), non-dopaminergic treatments as monotherapies were judged as a promising strategy to treat such a disease (Brotchie, J. M., *Curr. Opin. Neurol.*, 1997, 10, 340). Moreover, some scientific evidences also suggest that increased synthesis of adenosine $A_{2a}$ receptors in striatopallidal pathway neurons is associated with the development of dyskinesias following long-term levodopa therapy in Parkinson's disease (Calon, F., et al., *Brain*, 2004, 127, 1075; Xiao, D., et al., *J. Neurosci.*, 2006, 26, 52, 13548). $A_{2A}$ antagonists, in association with a low dose of L-DOPA, displayed antiparkinsonian activity similar to that produced by a full dose of L-DOPA without exacerbating abnormal motor side effects (Tronci E., et al. Eur *J. Pharmacol.*, 2007, 566, 94; Jenner P., *Expert Opin. Investig. Drugs*, 2005, 14, 6, 729).

Adenosine has also been implicated in numerous other pathologies such as epilepsy, cerebral ischaemic preconditioning, sleep and immune reaction within the brain (Brundege, J. M., et al., *Adv. Pharma.*, 1997, 39, 353).

Imidazopyrimidine derivatives of formula A as antidiabetic compounds are disclosed in patent U.S. RE39,112 E (Eisai Co., Ltd.).

Formula A wherein $R^1$ is

94% of the latter compounds (223 out of 237 exemplified compounds) present a fluoro-containing phenyl moiety as $R^3$ group and/or a tertiary alcohol within the $R^1$ radical, suggesting that those moieties constitute an important feature to confer the activity.

A patent (EP1412354) filed by the Applicant disclosed triazolyl-imidazopyridine and triazolylpurine derivatives endowed of anti-psychotic properties. However, none of the compounds of the present invention were neither disclosed nor suggested.

DESCRIPTION OF THE INVENTION

The invention provides novel compounds of formula I, or a hydrate or solvate thereof and compositions that include such compounds endowed with adenosine $A_{2a}$ inhibiting properties:

Formula I $R^1$ = is $C_1$-$C_6$ linear or branched alkyl;
$R^2$ is a group of formula $R^9$—$(CHR^8)_p$—$(CR^6R^7)_m$—$(CR^4R^5)_n$—;
$R^4$, $R^6$ and $R^8$ are at any occurrence independently H, hydroxyl or =O with the meaning of carbonyl;
$R^5$, $R^7$ and $R^9$ are at any occurrence independently H or are absent;
m, n and p are independently an integer comprised between 0 and 2;
m+n+p≥4;
$R^3$ is $NH_2$, $NHR^{10}$;
$R^{10}$ is $C_1$-$C_6$ alkyl or $C_1$-$C_6$ hydroxyalkyl, $C_1$-$C_3$ alkoxyalkyl, amino($C_1$-$C_6$)alkyl, where the amino group is optionally substituted with one or two $C_1$-$C_3$ alkyl groups, being said alkyl groups linear or branched; $C_6$-$C_{14}$ aryl or $C_6$-$C_{14}$ aryl($C_1$-$C_6$)alkyl, with the aryl group optionally substituted by one or more substituents, either the same or different, selected from the group constituted by halogen, hydroxy, $C_1$-$C_6$ alkoxy linear or branched saturated or unsaturated, amino, mono- or di-substituted with $C_1$-$C_6$ alkyl linear or branched;

their optically active forms such as enantiomers, diastereomers and their racemate forms, and pharmaceutically acceptable salts thereof;

with the proviso that $R^4$, $R^6$ and $R^8$ are not all H at the same time.

We have found that the derivatives (I), prepared according to the invention, are useful agents for the treatment of disease states, disorders and pathological conditions wherein modulation of the $A_{2A}$ receptor activity would result at improving the health of the patient.

An embodiment of this invention is that of compounds of formula I, for use as medicaments.

In another embodiment, said medicament is used for treating a subject affected by motor disorders deriving from functional alterations in the basal ganglia.

In a still further embodiment, said motor disorders consist of the ones involved in diseases comprising Parkinson's disease, Alzheimer's disease, Huntington's disease and Wilson's disease.

In another embodiment, the compounds of formula I are also useful for the preparation of medicaments for the treatment of cerebral ischaemia and/or associated with neurodegenerative processes.

The term "alkyl" refers to linear or branched alkyl groups having from 1 to 6 carbon atoms. Preferred alkyl groups are exemplified by groups such as methyl, ethyl, n-propyl, iso-propyl, n-butyl, isobutyl, neo-butyl, tert-butyl, pentyl, isopentyl, n-hexyl and the like.

The term "alkenyl" refers to linear or branched alkenyl groups preferably having from 2 to 12 carbon atoms, or preferably, 2 to 6 carbon atoms also named "lower" alkenyl group and having at least 1 or 2 sites of alkenyl unsaturation. Preferable alkenyl groups include ethenyl (—CH═CH2), propenyl (allyl, —CH₂CH═CH₂) and the like. The term alkenyl embraces radicals having "cis" and "trans" orientation, or alternatively "Z" and "E".

The term "cycloalkyl" refers to a saturated or partially unsaturated (i.e., not aromatic) carbocyclic group of from 3 to 10 carbon atoms having a single ring or multiple condensed rings. Examples of $C_3$-$C_{10}$ cycloalkyl include cyclopropyl, cyclobutyl, cyclopentyl, cyclohexyl, norbornyl, adamantyl and the like.

The term "heterocycloalkyl" refers to a saturated or partially unsaturated (i.e., not aromatic) five-, six- or seven-membered ring containing one or more heteroatoms selected from the group consisting of nitrogen, oxygen or sulfur atoms, and which rings may be substituted with lower alkyl, lower alkenyl, or aryl. Preferred heterocycloalkyl include pyrrolidine, piperidine, piperazine, ketopiperazine, 2,5-diketopiperazine, 1-methylpiperazine, morpholine, thiomorpholine, dihydropyranyl, tetrahydropyranyl, tetrahydrofuran, dihydropyrrole, imidazolidine, dihydropyrazole, pyrazolidine and the like.

The term "aryl" refers to an aromatic carbocyclic group of 6 to 14 carbon atoms having a single ring (e. g., phenyl) or multiple rings that may be attached in a pendent manner or may be fused. Preferred aryl include phenyl.

The term "alkoxy" refers to the group —O—R where R includes "$C_1$-$C_6$ alkyl", "$C_2$-$C_6$ alkenyl", "$C_3$-$C_{10}$ cycloalkyl" and "heterocycloalkyl".

The term "alkoxyalkyl" refers to alkyl groups as above defined having an alkoxy substituent as above defined, including 2-ethoxyethyl, methoxymethyl and the like.

The term "amino" refers to the group —NRR' where each R, R' is independently H, "alkyl", "alkenyl", "cycloalkyl", "heterocycloalkyl", "aryl", "heteroaryl" and where R and R', together with the nitrogen atom to which they are attached, can optionally form a 3 to 8-membered heterocycloalkyl ring as above defined.

The term "aminoalkyl" or "amino($C_1$-$C_6$)alkyl" refers to alkyl groups as above defined having an amino substituent as above defined.

"Pharmaceutically acceptable salts or complexes" refers to salts or complexes of the below identified compounds of formula (I), that retain the desired biological activity. Examples of such salts include, but are not restricted to acid addition salts formed with inorganic acids (e. g. hydrochloric acid, hydrobromic acid, sulfuric acid, phosphoric acid, nitric acid, and the like), and salts formed with organic acids such as acetic acid, oxalic acid, tartaric acid, succinic acid, malic acid, fumaric acid, maleic acid, ascorbic acid, benzoic acid, tannic acid, pamoic acid, alginic acid, polyglutamic acid, naphthalene sulfonic acid, toluene sulfonic acid, naphthalene disulfonic acid, methanesulfonic acid and poly-galacturonic acid. When the salt is of a mono acid (for example, the hydrochloride, the hydrobromide, the p-toluenesulphonate, or the acetate), the hydrogen form of a di-acid (for example, the hydrogen sulphate, or the succinate), or the dihydrogen form of a tri-acid (for example, the dihydrogen phosphate, or the citrate), at least one molar equivalent and usually a molar excess of the acid is employed. However, when such salts as the sulphate, the hemisuccinate, the hydrogen phosphate, or the phosphate are desired, the appropriate and exact chemical equivalents of acid are generally used.

"Pharmaceutically active derivative" refers to any compound that upon administration to the patient is capable of providing directly or indirectly, the activity disclosed herein.

The compounds according to formula I could be employed alone or in combination with further pharmaceutical agents such as L-DOPA.

The compounds of the present invention may be prepared from readily available starting materials using the following general methods and procedures. It will be appreciated that where typical or preferred experimental conditions (i. e., reaction temperatures, time, moles of reagents, solvents, etc.) are given, other experimental conditions can also be used unless otherwise stated. Optimum reaction conditions may vary with the particular reactants or solvents used, but such conditions can be determined by one skilled in the art by routine optimisation procedures.

When employed as pharmaceuticals, the compounds of the present invention are typically administered in the form of a pharmaceutical composition. Hence, pharmaceutical compositions comprising a compound of formula (I) and a pharmaceutically acceptable carrier, diluent or excipient therefore is also within the scope of the present invention. Such compositions can be prepared in a manner well known in the pharmaceutical art and comprise at least one active compound. A person skilled in the art is aware of a whole variety of such carrier, diluent or excipient compounds suitable to formulate a pharmaceutical composition.

The compounds of the present invention, together with a conventionally employed adjuvant, carrier, diluent or excipient may be placed into the form of pharmaceutical compositions and unit dosages thereof, and such forms may be employed as solids, such as tablets or filled capsules, or liquids such as solutions, suspensions, emulsions, elixirs, or capsules filled with the same, all for oral use, or in the form of sterile injectable solutions for parenteral (including subcutaneous use). Such pharmaceutical compositions and unit dosage forms thereof may comprise ingredients in conventional proportions, with or without additional active compounds or principles, and such unit dosage forms may contain any suitable effective amount of the active ingredient commensurate with the intended daily dosage range to be employed.

Generally, the compounds of this invention are administered in a "pharmaceutically effective amount". The amount of the compound actually administered will typically be determined by a physician, in the light of the relevant circumstances, including the condition to be treated, the chosen route of administration, the actual compound administered, drug combination, the age, body weight, and response of the individual patient, the severity of the patient's symptoms, and the like. Generally, an effective dose will be from 0.01 mg/kg to 100 mg/kg, preferably 0.05 mg/kg to 50 mg/kg. Compositions may be administered individually to a patient or may be administered in combination with other agents, drugs or hormones. For any compound, the therapeutically effective dose can be estimated initially either in cell culture assays or in animal models, usually mice, rats, guinea pigs, rabbits, dogs, or pigs.

The animal model may also be used to determine the appropriate concentration range and route of administration. Such information can then be used to determine useful doses and routes for administration in humans. In calculating the Human Equivalent Dose (HED) it is recommended to use the conversion table provided by the FDA in Guidance for Industry and Reviewers document available from FDA. The pharmaceutical compositions of this invention can be administered by a variety of routes including oral, rectal, sublingual, transdermal, subcutaneous, intravenous, intramuscular, intrathecal, intraperitoneal, intranasal and locally on the diseased tissue after surgical operation.

Depending on the intended route of delivery, the compounds are preferably formulated as parenteral, topical or oral compositions. The compositions for oral administration may take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include refilled, pre-measured ampoules or syringes of the liquid compositions or pills, tablets, capsules or the like in the case of solid compositions. In such compositions, the compound of the invention is usually a minor component (from about 0.1 to about 50% by weight or preferably from about 1 to about 40% by weight) with the remainder being various vehicles or carriers and processing aids helpful for forming the desired dosing form.

Dosage treatment may be a single dose schedule or a multiple dose schedule. Liquid forms suitable for oral administration may include a suitable aqueous or non-aqueous vehicle with buffers, suspending and dispensing agents, colorants, flavours and the like.

Solid forms may include, for example, any of the following ingredients, or compounds of a similar nature: a binder such as microcrystalline cellulose, acacia, gum tragacanth, gelatine or polyvinyl-pyrrolidone; an excipient such as starch or lactose, a disintegrating agent such as alginic acid, primogel, or potato or corn starch; a lubricant such as magnesium stearate, talc, polyethylene glycol or silica; a glidant such as colloidal silicon dioxide; a sweetening agent such as sucrose or saccharin; or a flavoring agent such as pepper-mint, methyl salicylate, or orange flavoring. The tablets may be coated according to methods well known to people skilled in the art of pharmaceutical practice.

Parenteral compositions are typically based upon injectable sterile saline or phosphate-buffered saline or other injectable carriers known in the art. As mentioned above, the compound of formula I in such compositions is typically a minor component, frequently ranging between 0.05 to 10% by weight with the remainder being the injectable carrier and the like.

The compounds of this invention can also be administered in sustained release forms or from sustained release drug delivery systems. A description of representative sustained release materials can also be found in the incorporated materials in Remington's Pharmaceutical Sciences.

The above-described components for orally administered or parenteral compositions are merely representative. Further materials as well as processing techniques and the like are set out in Part 5 of Remington's Pharmaceutical Sciences, 20$^{th}$ Edition, 2000, Mack Publishing Company, Easton, Pa., which is incorporated herein be reference.

A further embodiment of the invention is a process for the preparation of pharmaceutical compositions characterised by mixing one or more compounds of formula (I) with suitable excipients, stabilizers and/or pharmaceutically acceptable diluents.

As above disclosed, the compounds of the present invention are useful as medicaments due to their $A_{2a}$ modulating properties for the treatment of disorders where such modulation result in improving the health of the patient. In particular, patients suffering from Parkinson's disease, Alzheimer's disease, Huntington's disease, Wilson's disease, psychiatric disorders, Hallervorden-Spatz disease, progressive pallidal atrophy and diabetes can be treated.

Objects of the present invention are pharmaceutical compositions containing compounds of formula I, as described earlier, in combination with excipients and/or pharmacologically acceptable diluents.

A further embodiment of the invention is a process for the preparation of compounds of formula I as defined above. The compounds of the invention can be prepared by conventional synthetic methods and are described underneath.

Method A

Compounds of formula (I), wherein $R^1$ = is $C_1$-$C_6$ linear or branched alkyl;

$R^2$ is a group of formula $R^9$—$(CHR^8)_p$—$(CR^6R^7)_m$—$(CR^4R^5)_n$—;

$R^4$, $R^5$, $R^7$, and $R^9$ are H;

$R^6$ and $R^8$ are at any occurrence independently H or hydroxyl with at least one of them being hydroxyl;

m and p are independently an integer comprised between 0 and 2;

n is 1 or 2;

m+n+p≥4;

$R^3$ is $NH_2$, $NHR^{10}$; and

$R^{10}$ is $C_1$-$C_6$ alkyl or $C_1$-$C_6$ hydroxyalkyl, $C_1$-$C_3$ alkoxyalkyl, amino($C_1$-$C_6$)alkyl, where the amino group is optionally substituted with one or two $C_1$-$C_3$ alkyl groups, being said alkyl groups linear or branched; $C_6$-$C_{14}$ aryl or $C_6$-$C_{14}$ aryl($C_1$-$C_6$)alkyl, with the aryl group optionally substituted by one or more substituents, either the same or different, selected from the group constituted by halogen, hydroxy, $C_1$-$C_6$ alkoxy linear or branched saturated or unsaturated, amino, mono- or di-substituted with $C_1$-$C_6$ alkyl linear or branched;

can be synthesized by a process comprising the reaction of a compound of formula II

Formula II wherein
$R^1$ is $C_1$-$C_6$ linear or branched alkyl;
$R^{11}$ is $N(R^{13})_2$;
$R^{13}$ is benzyl, p-(MeO)-benzyl, p-(Cl)-benzyl or p-(Br)-benzyl;
$R^{12}$ is Cl;
with a compound of formula III Formula III, wherein,
X is Cl or Br;
$R^4$, $R^5$, $R^7$, and $R^9$ are H;
$R^{6a}$ and $R^{8a}$ are at any occurrence independently OH or H with at least one of them being OH;
m and p are independently an integer comprised between 0 and 2;
n is 1 or 2;
m+n+p≥4;
in the presence of Fe(acac)$_3$ in an aprotic solvent such as THF or NMP at a temperature ranging from 0° C. to RT.

Method B
Compounds of formula (I), wherein
$R^1$ is $C_1$-$C_6$ linear or branched alkyl;
$R^2$ is a group of formula $R^9$—(CHR$^8$)$_p$—(CR$^6$R$^7$)$_m$—(CR$^4$R$^5$)$_n$—;
$R^4$ and $R^5$ are H;
$R^6$ and $R^8$ are at any occurrence independently H or =O with the meaning of carbonyl; with at least one of $R^6$ and $R^8$ being =O with the meaning of carbonyl;
$R^7$ and $R^9$ are at any occurrence independently H, or are absent in case the corresponding carbon atom bearing said $R^6$ or $R^8$ group is involved in a carbonyl bond;
m and p are independently an integer comprised between 0 and 2;
n is 1 or 2;
m+n+p≥4;
$R^3$ is $NH_2$, $NHR^{10}$;
$R^{10}$ is $C_1$-$C_6$ alkyl or $C_1$-$C_6$ hydroxyalkyl, $C_1$-$C_3$ alkoxyalkyl, amino($C_1$-$C_6$)alkyl, where the amino group is optionally substituted with one or two $C_1$-$C_3$ alkyl groups, being said alkyl groups linear or branched; $C_6$-$C_{14}$ aryl or $C_6$-$C_{14}$ aryl($C_1$-$C_6$)alkyl, with the aryl group optionally substituted by one or more substituents, either the same or different, selected from the group constituted by halogen, hydroxy, $C_1$-$C_6$ alkoxy linear or branched saturated or unsaturated, amino, mono- or di-substituted with $C_1$-$C_6$ alkyl linear or branched;
can be synthesized by a process comprising the reaction of a compound of formula II as defined above, with a compound of formula IV

Formula IV, wherein
X is Cl or Br;
$R^{6b}$ and $R^{6c}$ are at any occurrence independently both H or when taken together with the carbon atom to which they are attached to form a 1,3-dioxane group optionally substituted by two or more methyl groups with at least one of the occurrence being a 1,3-dioxane group substituted by two or more methyl groups;
q is an integer comprised between 0 and 3;
r and s are independently an integer comprised between 1 and 3; with
q+r+s≥4;
in the presence of a Fe(acac)$_3$ in an aprotic solvent such as THF or NMP at a temperature ranging from 0° C. to RT.

Method C
Compounds of formula (I), wherein
$R^1$ is $C_1$-$C_6$ linear or branched alkyl;
$R^2$ is a group of formula $R^9$—(CHR$^8$)$_p$—(CR$^6$R$^7$)$_m$—(CR$^4$R$^5$)$_n$—;
$R^4$ is hydroxyl or =O with the meaning of carbonyl;
$R^5$ is H or is absent when $R^4$ is =O with the meaning of carbonyl;
$R^6$ and $R^8$ are at any occurrence independently H, hydroxyl or =O with the meaning of carbonyl;
$R^7$ and $R^9$ are at any occurrence independently H or are absent in case the corresponding carbon atom bearing said $R^6$ or $R^8$ group is involved in a carbonyl bond;
n is 1;
m and p are independently an integer comprised between 1 and 2, with m+p≥3;
$R^{10}$ is $C_1$-$C_6$ alkyl or $C_1$-$C_6$ hydroxyalkyl, $C_1$-$C_3$ alkoxyalkyl, amino($C_1$-$C_6$)alkyl, where the amino group is optionally substituted with one or two $C_1$-$C_3$ alkyl groups, being said alkyl groups linear or branched; $C_6$-$C_{14}$ aryl or $C_6$-$C_{14}$ aryl($C_1$-$C_6$)alkyl, with the aryl group optionally substituted by one or more substituents, either the same or different, selected from the group constituted by halogen, hydroxy, $C_1$-$C_6$ alkoxy linear or branched saturated or unsaturated, amino, mono- or di-substituted with $C_1$-$C_6$ alkyl linear or branched;
can be synthesized by a process comprising the following steps:
a) reaction of a compound of formula V Formula V wherein $R^1$ is $C_1$-$C_6$ linear or branched alkyl;
with i-PrMgCl;
b) in situ addition of compound formula VI Formula VI wherein:
$R^{6d}$ and $R^{7d}$ are at any occurrence independently H or OH with at least one of them being H; or
$R^{6d}$ and $R^{7d}$ when taken together with the carbon atom to which they are attached, form a 1,3-dioxane group optionally substituted by two or more methyl groups;
$R^{8d}$ is H or hydroxyl;
s and t are independently an integer comprised between 1 and 2, with s+t≥3;
in an aprotic solvent such as THF at a temperature ranging from −78° C. to RT.

Method D
  Compounds of formula (I), wherein
  $R^1$= is $C_1$-$C_6$ linear or branched alkyl;
  $R^2$ is a group of formula $R^9$—$(CHR^8)_p$—$(CR^6R^7)_m$—$(CR^4R^5)_n$—;
  $R^4$ and $R^5$ are H;
  $R^6$ and $R^8$ are at any occurrence independently H, hydroxyl or =O with the meaning of carbonyl;
  $R^7$ and $R^9$ are at any occurrence independently H or are absent in case the corresponding carbon atom bearing said $R^6$ or $R^8$ group is involved in a carbonyl bond;
  m and p are independently an integer comprised between 0 and 2;
  n=2;
  m+n+p≥4;
  $R^3$ is $NH_2$, $NHR^{10}$;
  $R_{10}$ is $C_1$-$C_6$ alkyl or $C_1$-$C_6$ hydroxyalkyl, $C_1$-$C_3$ alkoxyalkyl, amino($C_1$-$C_6$)alkyl, where the amino group is optionally substituted with one or two $C_1$-$C_3$ alkyl groups, being said alkyl groups linear or branched; $C_6$-$C_{14}$ aryl or $C_6$-$C_{14}$ aryl($C_1$-$C_6$)alkyl, with the aryl group optionally substituted by one or more substituents, either the same or different, selected from the group constituted by halogen, hydroxy, $C_1$-$C_6$ alkoxy linear or branched saturated or unsaturated, amino, mono- or di-substituted with $C_1$-$C_6$ alkyl linear or branched;
  can be synthesized by a process comprising the reaction of a compound of formula VII Formula VII wherein
  $R^1$= is $C_1$-$C_6$ linear or branched alkyl; with a compound of formula VIII Formula VIII wherein
  $R^6$ is at any occurrence independently H or hydroxyl,
  u is an integer equal to or greater than 2;
  in the presence of bis-triphenylphosphine palladium dichloride, CuI and optionally a tertiary amine such as triethylamine in a polar solvent such as dioxane at a temperature ranging from 0° C. to RT.
Method E
  Compounds of formula (I), wherein
  $R^1$= is $C_1$-$C_6$ linear or branched alkyl;
  $R^2$ is a group of formula $R^9$—$(CHR^8)_p$—$(CR^6R^7)_m$—$(CR^4R^5)_n$—;
  $R^4$, $R^6$ and $R^8$ are at any occurrence independently H, hydroxyl or =O with the meaning of carbonyl;
  $R^5$, $R^7$ and $R^9$ are at any occurrence independently H or are absent in case the corresponding carbon atom bearing said $R^4$, $R^6$ or $R^8$ group is involved in a carbonyl bond;
  m, n and p are independently an integer comprised between 0 and 2;
  m+n+p≥4;
  $R^3$ is $NH_2$, $NHR^{10}$;
  $R^{10}$ is $C_1$-$C_6$ alkyl or $C_1$-$C_6$ hydroxyalkyl, $C_1$-$C_3$ alkoxyalkyl, amino($C_1$-$C_6$)alkyl, where the amino group is optionally substituted with one or two $C_1$-$C_3$ alkyl groups, being said alkyl groups linear or branched; $C_6$-$C_{14}$ aryl or $C_6$-$C_{14}$ aryl($C_1$-$C_6$)alkyl, with the aryl group optionally substituted by one or more substituents, either the same or different, selected from the group constituted by halogen, hydroxy, $C_1$-$C_6$ alkoxy linear or branched saturated or unsaturated, amino, mono- or di-substituted with $C_1$-$C_6$ alkyl linear or branched;
  can be synthesized by a process comprising the reaction of compounds of formula II as above described with a compound of formula IX Formula IX wherein
  $R^{14}$ is at each occurrence independently H or OH;
  $R^{15}$ is H or OH;
  v is ≥2;
  in the presence of Hermann's catalyst and sodium acetate in a polar solvent such as NMP.
Method F
  Compounds of formula (I), wherein
  $R^1$= is $C_1$-$C_6$ linear or branched alkyl;
  $R^2$ is a group of formula $R^9$—$(CHR^8)_p$—$(CR^6R^7)_m$—$(CR^4R^5)_n$—;
  $R^4$ and $R^5$ are H;
  $R^6$ and $R^8$ are at any occurrence independently H, hydroxyl or =O with the meaning of carbonyl;
  $R^7$ and $R^9$ are at any occurrence independently H or are absent;
  m and p are independently an integer comprised between 0 and 2;
  n≥1;
  m+n+p≥4;
  $R^3$ is $NH_2$, $NHR^{10}$;
  $R^{10}$ is $C_1$-$C_6$ alkyl or $C_1$-$C_6$ hydroxyalkyl, $C_1$-$C_3$ alkoxyalkyl, amino($C_1$-$C_6$)alkyl, where the amino group is optionally substituted with one or two $C_1$-$C_3$ alkyl groups, being said alkyl groups linear or branched; $C_6$-$C_{14}$ aryl or $C_6$-$C_{14}$ aryl($C_1$-$C_6$)alkyl, with the aryl group optionally substituted by one or more substituents, either the same or different, selected from the group constituted by halogen, hydroxy, $C_1$-$C_6$ alkoxy linear or branched saturated or unsaturated, amino, mono- or di-substituted with $C_1$-$C_6$ alkyl linear or branched;
  can be synthesized by a process comprising the reaction of compounds of formula VII as above described with a compound of formula X $$R^9\text{—}(CHR^8)_p\text{—}(CR^{6d}R^{7d})_m\text{—}(CR^4R^5)_n\text{—}ZnBr \qquad \text{Formula X};$$

wherein
  $R^4$ and $R^5$ are H;
  $R^{6d}$ and $R^{7d}$ are at any occurrence independently H or OH with at least one of them being H; or $R^{6d}$ and $R^{7d}$ when taken together with the carbon atom to which they are attached, form a 1,3-dioxane group optionally substituted by two or more methyl groups;

$R^8$ is at any occurrence independently H or hydroxyl;

$R^9$ is H;

m and p are independently an integer comprised between 0 and 2;

n≥1;

m+n+p≥4;

in a polar solvent such as THF.

In all said transformations, any interfering reactive group can be protected and then deprotected according to well-established procedures described in organic chemistry (see for example: Greene T. W. and P. G. M. Wuts "Protective Groups in Organic Synthesis", J. Wiley & Sons, Inc., 3rd Ed., 1999) and well known to those skilled in the art.

EXAMPLES

Abbreviations

AcOEt: ethyl acetate
atm: atmosphere
bs: broad singlet
DCM: dichloromethane
DMEM: Dulbecco's modified eagle's medium
DMSO: dimethylsyulfoxide
EDTA: ethylenediaminetetraacetic acid
$Et_2O$: diethyl ether
FBS: foetal Bovine Serum
MeOH: methanol
$MgCl_2$: magnesium dichloride
MS: mass spectrum
$Na_2SO_4$: sodium sulphate
$NEt_3$: triethyl amine
NMP: N-methyl pyrrolidinone
PBS: phosphate-buffered saline
PCC: pyridinium chlorochromate
RP-HPLC: reversed phase-high-performance liquid chromatography
Rt: retention time
RT: room temperature
TfOH: Trifluoromethanesulfonic acid General Remarks: $^1$H spectra were recorded in $CDCl_3$ or DMSO-$d_6$ solution as indicated, at 200 MHz with a Bruker instrument. The chemical shift values are given in ppm and the coupling constants in Hz. Flash column chromatography was carried out using silica gel (Merck 230-400 mesh). Chiral chromatography was performed using a HPLC Shimadzu LC-10AS chromatograph connected with a Vis-UV SPD 10A Shimadzu detector and a Shimadzu C-R6A chromatopak integrator. The stationary phase consisted of a Chiralpak AD-H column, Daicel Chemical industries (Chiral France) [Amylose tris(3,5-dimethylphenylcarbamate) coated on 5 mm silica-gel] of diameter 0.46 cm, length 25 cm. The mobile phase consisted of n-hexane/2-propanol: 9/1 at a flow equal to 1 ml/min, λ 289 nm.

Example 1

4-(6-Amino-9-methyl-8[1,2,3]triazol-2-yl-9H-purin-2-yl)butan-1-ol (ST4023)

Step A: 4-(6-Chloro-9-methyl-9H-purin-2-yl)but-3-yn-1-ol $NEt_3$ (4.9 ml, 34.5 mmol) and but-3-yn-1-ol (1.1 ml, 25.63 mmol) were added to a solution of 6-chloro-2-iodo-9-methyl-9H-purine (6.8 g, 23.3 mmol), CuI (454 mg, 2.23 mmol) and bis-triphenylphosphine palladium dichloride (811 mg, 1.15 mmol) in dioxane (93 ml). The reaction mixture was stirred at RT for 1 h. The solvents were removed under reduced pressure. Water (50 ml) was added to the dark residue obtained. The aqueous phase was extracted with DCM (3×100 ml). The combined organic phases were dried over anhydrous sodium sulphate and evaporated under reduced pressure. The residue was purified by flash chromatography (DCM/MeOH: 94/6) to give an off-white precipitate.

Yield 77%.

$^1$H NMR (DMSO-$d_6$) δ: 2.67 (t, 2H, J=6.82 Hz), 3.68 (t, 2H, J=6.82 Hz), 3.86 (s, 3H), 5.01 (bs, 1H), 8.68 (s, 1H).

$^{13}$C NMR (DMSO-$d_6$) δ: 23.33, 30.63, 59.62, 80.55, 88.11, 130.42, 144.73, 148.86, 149.28, 152.79

MS(ESI) m/e: 237-239 $(M+H)^+$

Step B: 4-(6-Amino-9-methyl-9H-purin-2-yl)but-3-yn-1-ol

To a solution of 4-(6-chloro-9-methyl-9H-purin-2-yl)but-3-yn-1-ol (650 mg, 2.74 mmol) in dioxane (4 ml) was added 30% w/w water solution of ammonia (8 ml). The reaction mixture was stirred overnight in an autoclave at 70° C.

The solution was evaporated at atmospheric pressure at 50° C. to remove the ammonia. The reaction mixture was maintained at RT for 2 h, to give a white precipitate. The solid was filtered and dried under vacuum.

Yield 78%.

$^1$H NMR (DMSO-$d_6$) δ: 2.52 (t, 2H, J=6.82 Hz), 3.58 (dt, 2H, J=6.82 Hz, J=5.5 Hz), 3.68 (s, 3H), 4.90 (t, 1H, J=5.5 Hz), 7.25 (bs, 2H), 8.09 (s, 1H).

$^{13}$C NMR (DMSO-$d_6$) δ: 23.24, 29.84, 59.95, 82.23, 83.46, 118.51, 142.58, 146.01, 150.38, 156.05

MS(ESI) m/e: 218 $(M+H)^+$

Step C: 4-(6-Amino-9-methyl-9H-purin-2-yl)butan-1-ol

To a solution of 4-(6-amino-9-methyl-9H-purin-2-yl)-but-3-yn-1-ol (1.5 g, 6.88 mmol) in ethanol (30 ml) was added palladium 10% on graphite (1.35 g, 20% in weight). The mixture was stirred for 16 h in autoclave at 50° C. under 4 atm of hydrogen. The catalyst was filtered through a small pad of Celite and the solution obtained was evaporated under reduced pressure, to give a residue that was used for the following reaction without further purification.

Yield 70%.

$^1$H NMR (DMSO-$d_6$) δ: 1.49 (m, 2H), 1.70 (m, 2H), 2.55 (t, 2H), 3.39 (m, 2H), 3.67 (s, 3H), 4.34 (bs, 1H), 7.01 (s, 2H), 7.97 (s, 1H).

$^{13}$C NMR (DMSO-$d_6$) δ: 25.54, 29.68, 32.85, 39.04, 61.09, 117.39, 141.33, 151.04, 156.05, 164.93

MS(ESI) m/e: 222.0 (M+H)+

Step D: 4-(6-Amino-8-bromo-9-methyl-9H-purin-2-yl)butan-1-ol

Bromine (0.4 ml, 6.8 mmol) was added dropwise, at −14° C., to 4-(6-amino-9-methyl-9H-purin-2-yl)butan-1-ol (250 mg, 1.13 mmol) dissolved in a mixture of dioxane (5 ml) and acetate buffer pH 4 (2.5 ml) (obtained by dissolving 4 g of sodium acetate in 100 ml of water and by adjusting to pH 4 with glacial acetic acid). The reaction was stirred at this temperature for 10 minutes and then at RT for 15 minutes. Excess of bromine was eliminated with sodium metabisulphite and the reaction brought to pH 8 by addition of saturated solution of $Na_2CO_3$. The aqueous phase was extracted with DCM (6×10). The organic phases were dried over anhydrous sodium sulphate and evaporated under reduced pressure, to give a residue that was used for the following reaction without further purification.

Step E: 4-(6-Amino-9-methyl-8[1,2,3]triazol-2-yl-9H-purin-2-yl)butan-1-ol (ST4023)

To a solution of 4-(6-amino-8-bromo-9-methyl-9H-purin-2-yl)butan-1-ol (1.4 g, 4.56 mmol) in anhydrous DMF (20 ml) were added $Cs_2CO_3$ (5.9 g, 18.24 mmol) and then 1H-1,2,3-triazole (1.2 g, 1.0 ml, 17.2 mmol). The mixture was stirred overnight at 90° C. The solvent was evaporated under reduced pressure to give a residue that was purified by flash chromatography (DCM/MeOH: 93/7).

Yield 30%.

$^1$H NMR (DMSO-$d_6$) δ: 1.46 (m, 2H), 1.73 (m, 2H), 2.67 (t, 2H, J=7.5 Hz), 3.38 (m, 2H), 3.76 (s, 3H), 4.38 (bs, 1H), 7.38 (s, 2H), 8.31 (s, 2H).

$^{13}$C NMR (DMSO-$d_6$) δ: 25.43, 30.65, 32.80, 39.15, 61.04, 114.92, 138.06, 141.42, 151.14, 156.17, 166.17

MS(ESI) m/e: 289 (M+H)$^+$

Example 2

4-(6-Amino-9-methyl-8[1,2,3]triazol-2-yl-9H-purin-2-yl)butan-2-ol (ST3932)

Step A: 4-(6-Chloro-9-methyl-9H-purin-2-yl)but-3-yn-2-ol

To a solution of 6-chloro-2-iodo-9-methyl-9H-purine (6.8 g, 23.3 mmol), CuI (454 mg, 2.23 mmol) and bis-triphenylphosphine palladium dichloride (811 mg, 1.15 mmol) in dioxane (93 ml) were added triethylamine (4.9 ml, 34.5 mmol) and but-3-yn-2-ol (1.1 ml, 25.63 mmol). The reaction mixture was stirred at RT for 1 h. The volatiles were removed under reduced pressure. Water (50 ml) was added to the dark residue obtained. The aqueous phase was extracted with DCM (3×100 ml). The combined organic phases were dried over anhydrous sodium sulphate and evaporated under reduced pressure. The combined organic phases were dried over anhydrous sodium sulphate and evaporated under reduced pressure. The residue was purified by flash chromatography (DCM/MeOH: 94/6).

Yield 77%.

$^1$H NMR (CDCl$_3$) δ: 1.62 (d, 3H, J=6.67 Hz), 3.95 (s, 3H), 4.81 (q, 1H, J=6.64), 8.17 (bs, 1H).

$^{13}$C NMR (CDCl$_3$) δ: 23.52, 29.72, 57.31, 81.41, 89.94, 130.59, 144.75, 148.20, 149.21, 152.65.

MS(ESI) m/e: 237-239 (M+H)$^+$

Step B: 4-(6-Amino-9-methyl-9H-purin-2-yl)but-3-yn-2-ol

To a solution of 4-(6-chloro-9-methyl-9H-purin-2-yl)but-3-yn-2-ol (4.8 g, 20.34 mmol) in dioxane (30 ml) was added 30% w/w water solution of ammonia (60 ml). The reaction mixture was stirred overnight in an autoclave at 70° C. The solution was evaporated at atmospheric pressure at 50° C. and then under reduced pressure. The residue was purified by flash chromatography (DCM/MeOH: 97/3).

Yield 78%.

$^1$H NMR (DMSO-$d_6$) δ: 1.42 (d, 3H, J=6.67 Hz), 3.75 (s, 3H), 4.61 (q, 1H), 5.71 (bs, 1H), 7.42 (bs, 2H) 8.17 (s, 1H).

$^{13}$C NMR (DMSO-$d_6$) δ: 24.75, 29.89, 56.83, 83.14, 87.63, 130.01, 142.74, 145.65, 150.28, 156.07

MS(ESI) m/e: 218 (M+H)$^+$

Step C: 4-(6-Amino-9-methyl-9H-purin-2-yl)butan-2-ol 4-(6-Amino-9-methyl-9H-purin-2-yl)but-3-yn-2-ol (1.5 g, 6.88 mmol) was placed in an autoclave with ethanol (30 ml) and palladium 10% on graphite (0.350 g, 20% in weight) was added. The mixture was stirred overnight under 4 atm of hydrogen at 50° C. The catalyst was filtered off through Celite and the resulting solution was evaporated under reduced pressure, to give a residue that was used without any further purification.

Yield 70%.

$^1$H NMR (CD$_3$OD) δ: 1.21 (d, 3H, J=6.32 Hz), 1.9 (m, 2H), 2.85 (m, 2H), 3.35 (bs, 2H), 3.84 (s, 3H), 3.89 (m, 1H), 8.00 (s, 1H).

$^{13}$C NMR (CD$_3$OD) δ: 22.01, 28.72, 34.97, 37.72, 66.89, 116.59, 141.54, 150.37, 155.56, 165.42

MS(ESI) m/e: 222 (M+H)$^+$

Step D: 4-(6-Amino-8-bromo-9-methyl-9H-purin-2-yl)butan-2-ol

Bromine (2.1 ml, 41 mmol) was added dropwise at −14° C. to a solution of 4-(6-amino-9-methyl-9H-purin-2-yl)butan-2-ol (800 mg, 3.60 mmol) in a mixture of MeOH/THF (20 ml, 1/1) and acetate buffer pH=4 (10 ml). The latter was obtained dissolving 4 g of sodium acetate in 100 ml of water and by adjusting to pH 4 through addition of glacial acetic acid. The reaction was stirred at this temperature for 10 minutes and then at RT for 10 minutes. Excess of bromine was quenched by addition of sodium metabisulphite and the reaction was brought to pH 8 by addition of a saturated solution of $Na_2CO_3$. The organic solvents were evaporated under reduced pressure, to give a solid that was filtered and used without any further purification.

Yield 76%.

Step E: 4-(6-Amino-9-methyl-8-[1,2,3]triazol-2-yl-9H-purin-2-yl)butan-2-ol (ST3932)

To a solution of 4-(6-amino-8-bromo-9-methyl-9H-purin-2-yl)butan-2-ol (1.4 g, 4.56 mmol) in anhydrous DMF (20 ml) were added CsCO$_3$ (5.9 g, 18.24 mmol) and 1H-1,2,3-triazole (1.2 g, 1.0 ml, 18.24 mmol). The mixture was stirred overnight at 90° C. The solvent was evaporated under reduced pressure to give a residue that was purified by flash chromatography (DCM/MeOH: 93/7).

Yield 27%.

¹H NMR (DMSO-d₆) δ: 1.09 (d, 3H, J=6.2 Hz), 1.78 (m, 2H), 2.72 (m, 2H), 3.66 (m, 1H), 3.77 (s, 3H), 4.45 (bs, 1H), 7.32 (bs, 2H), 8.29 (s, 2H).
¹³C NMR (DMSO-d₆) δ: 24.0, 30.6, 35.9, 38.5, 66.2, 114.9, 138.0, 141.4, 151.2, 156.2, 166.4
MS(ESI) m/e: 289 (M+H)⁺

Example 3

(S)-4-(6-Amino-9-methyl-8-[1,2,3]triazol-2-yl-9H-purin-2-yl)butan-2-ol (ST5748)

This compound was prepared according to the procedure described in Example 2, using (S)-(–)-but-3-yn-2-ol in STEP 1 instead of its racemate. In STEP E, the crude reaction mixture was purified by flash chromatography (DCM/MeOH: 95/5).
HPLC: Rt: 29 mn Example 4

(R)-4-(6-Amino-9-methyl-8-[1,2,3]triazol-2-yl-9H-purin-2-yl)butan-2-ol (ST5749)

This compound was prepared according to the procedure described in Example 2, using (R)-(–)-but-3-yn-2-ol in STEP 1 instead of its racemate. In STEP E, the crude reaction mixture was first purified by flash chromatography (DCM/MeOH: 95/5).
HPLC: Rt: 26 mn Example 5

1-(6-Amino-9-methyl-8-[1,2,3]triazol-2-yl-9H-purin-2-yl)butan-1-ol (ST3829)

Step A: 1-(6-Chloro-9-methyl-9H-purin-2-yl)butan-1-ol

To a solution of 6-chloro-2-iodo-9-methyl-9H-purine (3.7 g, 12.6 mmol) in anhydrous THF (48 ml) at −78° C. under an atmosphere of nitrogen was added isopropylmagnesium chloride (8 ml, 15.12 mmol). After 30 minutes butyraldehyde (1.7 ml, 16.38 mmol) was added at −78° C. dropwise. The reaction mixture was stirred at −78° C. for 8 h and then allowed to warm to RT overnight. The reaction was quencend with a saturated solution of NH₄Cl. The aqueous phase was extracted with DCM (three times). The organic phases were dried over anhydrous sodium sulphate and evaporated under reduced pressure. The residue was purified by flash chromatography (gradient DCM/MeOH: 98/2 to DCM/MeOH: 96/4).
Yield 59%.
¹H NMR (CD₃OD) δ: 0.96 (t, 3H, J=7.34), 1.45 (m, 2H), 1.86 (m, 2H), 3.95 (s, 3H), 4.83 (t, 1H, J=6.5), 8.47 (s, 1H).
¹³C NMR (CD₃OD) δ: 12.85, 18.41, 29.22, 38.90, 73.80, 129.13, 147.46, 149.6, 152.53, 166.27.
MS (ESI+): 241-243 (M+H)⁺

STEP B: 1-(6-Amino-9-methyl-9H-purin-2-yl)butan-1-ol

To the solution of 1-(6-chloro-9-methyl-9H-purin-2-yl)butan-1-ol (1.8 g, 7.47 mmol) in dioxane (10 ml) was added 30% w/w water solution of ammonia (20 ml). The reaction mixture was stirred overnight in an autoclave at 70° C. The solution was evaporated at atmospheric pressure at 50° C. and then under reduced pressure. The residue was purified by flash chromatography (DCM/MeOH: 95/5).
Yield 80%.
¹H NMR (DMSO-d₆) δ: 0.93 (t, 3H, J=7.06), 1.40 (m, 2H), 1.78 (m, 2H), 3.77 (s, 3H), 4.48 (m, 1H), 4.84 (d, 1H), 7.31 (s, 2H), 8.12 (s, 1H).
¹³C NMR (DMSO-d₆) δ: 14.95, 19.37, 30.29, 39.99, 73.86, 118.35, 142.33, 151.18, 156.52, 166.43.
MS (ESI+): 222 (M+H)⁺

Step C: 1-(6-Amino-8-bromo-9-methyl-9H-purin-2-yl)butan-1-ol

Bromine (3.6 ml, 70.4 mmol) was added dropwise, at −14° C., to 1-(6-amino-9-methyl-9H-purin-2-yl)butan-1-ol (1700 mg, 7.69 mmol) dissolved in a mixture of MeOH (20 ml), THF (20 ml) and acetate buffer pH 4 (20 ml) (obtained by dissolving 4 g of sodium acetate in 100 ml of water and by adjusting pH 4 with glacial acetic acid). The reaction was stirred at this temperature for 15 minutes and then at RT for 10 minutes. Excess of bromine was eliminated with sodium metabisulphite and the reaction brought to pH 8 by addition of saturated solution of Na₂CO₃. The organic solvents were evaporated under reduced pressure, to give a solid that was filtered and used for the following reaction without further purification.
Yield 82%.

Step D: 1-(6-Amino-9-methyl-8-[1,2,3]triazol-2-yl-9H-purin-2-yl)butan-1-ol (ST3829)

To the solution of 1-(6-amino-8-bromo-9-methyl-9H-purin-2-yl)-butan-1-ol (1.4 g, 4.56 mmol) in anhydrous DMF (20 ml) were added CsCO₃ (5.9 g, 18.24 mmol) and then 1H-1,2,3-triazole (1.2 g, 1.0 ml, 18.24 mmol). The mixture was stirred overnight at 90° C. The solvent was evaporated under reduced pressure to give a residue that was purified by flash chromatography (DCM/MeOH: 93/7).
Yield 30%.
¹H NMR (DMSO-d₆) δ: 0.92 (t, 3H, J=7.18), 1.40 (q, 2H, J=8.2), 1.75 (m, 2H), 3.86 (s, 3H), 4.50 (m, 1H), 4.88 (d, 1H), 7.58 (bs, 1H), 8.37 (s, 2H).
¹³C NMR (DMSO-d₆) δ:14.94, 19.37, 31.34, 39.88, 74.06, 115.90, 138.63, 142.27, 151.42, 156.64, 167.72.
MS (ESI+): 289 (M+H)⁺

Example 6

1-(6-Amino-9-methyl-8-[1,2,3]triazol-2-yl-9H-purin-2-yl)-butan-1-one ST4208

MnO₂ (439 mg, 5.04 mmol) was added to a solution of 1-(6-amino-9-methyl-8-[1,2,3]triazol-2-yl-9H-purin-2-yl)butan-1-ol (51 mg, 0.2 mmol) in DCM (4 ml) at RT. The resulting heterogeneous solution was stirred overnight. After filtration over a celite pad, the solvent was removed under reduced pressure to afford the desired product as a white powder.
Yield 40%.
¹H NMR (DMSO-d₆) δ: 8.4 (s, 2H), 7.7 (bs, 2H), 3.9 (s, 3H), 3.14 (t, 2H), 1.66 (m, 2H), 0.95 (t, 3H)
ESI-MS (m/z): 287.1 (M+H)⁺

Example 7

4-(6-Amino-9-methyl-8[1,2,3]triazol-2-yl-9H-purin-2-yl)-butan-2-one ST4206

Molecular sieves 4 Å (100 mg) and PCC (59 mg, 0.273 mmol) at 0° C. were added to a solution of 4-(6-amino-9- methyl-8[1,2,3]triazol-2-yl-9H-purin-2-yl)-butan-2-ol (25 mg, 0.086 mmol) in DCM (1.2 ml). The mixture was stirred at RT for 1 h and then diluted with Et$_2$O at 0° C. and stirred for 30 minutes. The resulting suspension was filtered through a celite pad. The filtrate was concentrated in vacuo and the residue was purified by silica gel column chromatography (DCM to DCM/MeOH: 95/5) to afford a white powder.

Yield 37%.

$^1$H NMR (CD$_3$CN) δ: 8.1 (s, 2H), 5.9 (bs, 2H), 3.8 (s, 3H), 3.07 (t, 2H), 2.9 (t, 2H), 2.2 (s, 3H).

ESI-MS (m/z): 287.1 (M+H)$^+$

In alternative, 4-(6-amino-9-methyl-8[1,2,3]triazol-2-yl-9H-purin-2-yl)-butan-2-one can be prepared from an advanced intermediate obtained by a process involving Method B as above mentioned and as described underneath.

Preparation 1

4-(6-Amino-9-methyl-8-[1,2,3]triazol-2-yl-9H-purin-2-yl)-butan-2-one (ST4206)

Step A: Dibenzyl-{9-methyl-2-[2-(2,5,5-trimethyl-[1,3]dioxan-2-yl)-ethyl]-9H-purin-6-yl}-amine i) 1,2-dibromoethane (770 μl, 8.9 mmol) was added to a suspension of Mg (3.1 g, 127.5 mmol) in THF (75 ml) in inert atmosphere (Ar). Then, a solution of 2-(2-bromoethyl)-2,5,5-trimethyl-1,3-dioxane (8.0 ml, 42.5 mmol) and 1,2-dibromoethane (3.08 ml, 36 mmol) in THF (75 ml) was added, and after the exothermic reaction was completed, the resulting reaction mixture was heated to 50° C. for 1 h.

ii) Fe(acac)$_3$ (315 mg, 0.89 mmol) was added to a solution of dibenzyl-(2-chloro-9-methyl-9H-purin-6-yl)-amine (3.24 g, 8.9 mmol) in THF (115 ml) and NMP (28.5 ml) and the resulting reaction mixture was stirred at RT for 30 min. 140 ml of the freshly prepared reagent obtained from STEP A (i) were added to the reaction mixture and the stirring was maintained for 1 h. The solvent was removed under reduced pressure, and the crude reaction mixture was poured into water and extracted by means of AcOEt. The combined organic phases were washed with brine and dried with Na$_2$SO$_4$. After removal of the solvent under reduced pressure, the desired adduct was obtained quantitatively as a brown oil.

$^1$H NMR (CDCl$_3$) δ: 0.85 (s, 3H), 1.00 (s, 3H), 1.30 (s, 3H), 1.89-2.00 (m, 2H), 2.85-2.91 (m, 2H), 3.47-3.61 (m, 4H), 3.80 (s, 3H), 4.91 (brs, 2H), 5.40 (brs, 2H), 7.2-7.4 (m, 10H), 7.66 (s, 1H).

ESI-MS (m/z): 486 (M+H)$^+$

Step B: Dibenzyl-{8-bromo-9-methyl-2-[2-(2,5,5-trimethyl-[1,3]dioxan-2-yl)-ethyl]-9H-purin-6-yl}amine Bromine (0.89 ml, 17.5 mmol) was added dropwise at 0° C. to a solution of dibenzyl-{9-methyl-2-[2-(2,5,5-trimethyl-[1,3]dioxan-2-yl)-ethyl]-9H-purin-6-yl}-amine (1.7 g, 3.50 mmol) in 20 ml of a mixture of MeOH/THF (1/1) and acetate buffer pH=4 (10 ml). The latter was obtained dissolving 4 g of sodium acetate in 100 ml of water and by adjusting to pH 4 through addition of glacial acetic acid. The reaction was stirred at RT for two hours. Excess of bromine was quenched by addition of sodium metabisulphite and the reaction was brought to pH 8 by addition of a saturated solution of Na$_2$CO$_3$. The organic solvents were evaporated under reduced pressure, to give a solid that was filtered and used without any further purification in the next step.

$^1$H NMR (CDCl$_3$) δ: 0.85 (s, 3H), 1.00 (s, 3H), 1.30 (s, 3H), 1.89-2.00 (m, 2H), 2.82-2.89 (m, 2H), 3.47-3.61 (m, 4H), 3.75 (s, 3H), 4.91 (bs, 2H), 5.40 (bs, 2H), 7.20-7.40 (m, 10H).

ESI-MS (m/z): 564-566 (M+H)$^+$

Step C: Dibenzyl-{9-methyl-8-[1,2,3]triazol-2-yl-2-[2-(2,5,5-trimethyl-[1,3]dioxan-2-yl)-ethyl]-9H-purin-6-yl}-amine To a solution of dibenzyl-{8-bromo-9-methyl-2-[2-(2,5,5-trimethyl-[1,3]dioxan-2-yl)-ethyl]-9H-purin-6-yl}amine (1.9 g, 3.50 mmol) in anhydrous DMF (20 ml) were added K$_2$CO$_3$ (0.72 g, 5.2 mmol) followed by 1H-1,2,3-triazole (362 mg, 5.2 mmol). The mixture was stirred overnight at 100° C. The solvent was evaporated under reduced pressure to give a residue that was purified by flash chromatography (DCM/MeOH: 93/7).

Yield 30%.

1H NMR (CDCl$_3$) δ: 0.85 (s, 3H), 1.00 (s, 3H), 1.30 (s, 3H), 1.89-2.00 (m, 2H), 2.79-2.83 (m, 2H), 3.47-3.61 (m, 4H), 3.90 (s, 3H), 4.91 (brs, 2H), 5.40 (bs, 2H), 7.2-7.4 (m, 10H), 8.00 (s, 2H).

MS(ESI) m/e: 553 (M+H)$^+$

Step D: 4-(6-Amino-9-methyl-8-[1,2,3]triazol-2-yl-9H-purin-2-yl)-butan-2-one (ST4206)

The intermediate obtained form STEP C, was deprotected using standard TfOH conditions, which after chromatography on silica gel allowed the obtention of the desired adduct quantitatively.

1H NMR (CD3CN) δ: 8.10 (s, 2H), 5.90 (bs, 2H), 3.80 (s, 3H), 3.07 (t, 2H), 2.90 (t, 2H), 2.20 (s, 3H).

ESI-MS (m/z): 287 (M+H)$^+$

In alternative, 4-(6-amino-9-methyl-8[1,2, 3]triazol-2-yl-9H-purin-2-yl)-butan-2-one can be prepared from an advanced intermediate obtained by a process involving Method E as above mentioned and as described underneath.

Preparation 2

Hermann catalyst (8 mg, 0.008 mmol, 0.08 eq), Bu$_4$NBr (8 mg, 0.025 mmol, 0.25 eq), NaOAc (9 mg, 0.11 mmol, 1.1 eq) and 3-buten-2-ol (13 μl, 0.15 mmol, 1.5 eq) were added to a solution of (2-chloro-9-methyl-8[1,2,3]triazol-2-yl-9H-purin-6-yl)-bis-(4-methoxy-benzyl)-amine (49 mg, 0.10 mmol) in NMP (1 ml). The resulting reaction mixture was heated to 100° C. for 16 h and further Hermann catalyst, Bu$_4$NBr, and NaOAc were added in the same proportions together with further 3 eq of 3-buten-2-ol. The stirring was continued for 22 h at 140° C. before cooling to RT. The resulting crude suspension was diluted with AcOEt and the solid was filtered off. The organic phase was washed with H$_2$O and then dried over Na$_2$SO$_4$. Removal of the solvent under vacuo and purification through preparative thin layer chromatography allowed the obtention as a white solid of the desired 4-{6-[bis-(4-methoxy-benzyl)-amino]-9-methyl-8-[1,2,3]triazol-2-yl-9H-purin-2-yl}-butan-2-one.

Yield 42%.

$^1$H NMR (CDCl$_3$) δ: 2.12 (s, 3H), 2.94 (t, 2H), 3.16 (t, 2H), 3.78 (s, 6H), 3.94 (s, 3H), 4.85 (bs, 2H), 5.39 (bs, 2H), 6.82 (d, 4H), 7.18 (d, 4H), 7.94 (s, 2H).

Biology

The compounds of the present invention were tested in a competition binding assay for their ability to inhibit A$_{2a}$ receptor.

Example 8

$A_{2a}$ Receptor Inhibition

Method

HEK293 Cell Culture and Membrane Preparation

HEK293 cells, stably expressing the human adenosine $A_{2a}$ receptor gene (PerkinElmer, Boston, Mass., USA, cat. RBHA2AC), were grown in Falcon flasks in DMEM (Cambrex, Verviers, Belgium) supplemented with 10% FBS (Cambrex), 1 mmol/l sodium pyruvate (Sigma-Aldrich, Saint Louis, Mo., USA), 0.4 mg/ml G418 (Sigma-Aldrich) at 37° C. in a 5% $CO_2$ atmosphere. For radioligand binding experiments, the cells were collected at 80% of confluence, in 5 mmol/l Tris-HCl (Sigma-Aldrich), pH 7.4, containing 2 mmol/l EDTA, counted, washed in PBS (Cambrex), resuspended in incubation buffer A containing 50 mmol/l Tris-HCl, pH 7.4, 10 mmol/l $MgCl_2$ (Sigma-Aldrich) and homogenized using an Ultra Turrax T25. The membranes were centrifuged and homogenized once again and the final pellet was stored at −80° C. until use. Prior to the competition binding assay, the pellet was resuspended in buffer A at the desired protein concentration and membrane suspension was incubated with 2 U/ml adenosine deaminase (ADA, Sigma-Aldrich) for 30 min at 37° C. to remove endogenous adenosine.

Protein Concentration and Competition Binding Assay

The protein concentration of membrane suspension was determined using the Bradford method (Pierce, Rockford, Ill., USA) with bovine albumin as standard. Competition binding experiments were performed by incubating membranes (5-10 μg of protein/sample) with a single concentration of the $A_{2a}$ antagonist [$^3$H]ZM241385 (Biotrend, Cologne, Germany) (2 nmol/l), in the presence of various concentrations (ranging from $10^{-5}$ to $10^{-11}$ mol/l) of test and reference compounds in 96-well filter plates (MultiScreen system, cat. MAFBN0B10, Millipore, Billerica, Mass., USA) for one h at 4° C. in a total volume of 200 μl/well of appropriate buffer (50 mmol/l Tris-HCl, pH 7.4, 10 mmol/l $MgCl_2$). Nonspecific binding was determined in the presence of 10 μmol/l cold ZM241385 (Tocris, Ellisville, Mo., USA). At the end of incubation, bound and free radioligands were separated by filtering the 96-well filter plates using a Millipore filtration apparatus (MultiScreenHTS vacuum manifold). Filter plates were then washed several times with ice-cold buffer (50 mmol/l Tris-HCl, pH 7.4) and filter-bound radioactivity measured using a MicroBeta counter (PerkinElmer) after addition of 30 μl/well of OptiPhase SuperMix scintillation cocktail (PerkinElmer). Four experiments were performed in triplicate by JANUS® automated workstation (Perkin Elmer).

Data were analyzed by nonlinear regression analysis with GraphPad PRISM commercial software and expressed as $IC_{50}$, defined as the concentration of compounds that inhibits 50% of [$^3$H]ZM241385 binding. Inhibitory binding constant (Ki) values were calculated from $IC_{50}$ values according to the Cheng and Prusoff equation $Ki=IC_{50}/(1+[C]/Kd)$, where [C] is the concentration of the radioligand and Kd its dissociation constant.

Results

All tested compounds proved to be highly active in binding $A_{2A}$ receptor assay (table 1).

TABLE 1

| Examples | $A_{2A}$ Ki nM |
|---|---|
| 1 | 53 |
| 2 | 8 |
| 3 | 19 |
| 4 | 8 |
| 5 | 22 |
| 6 | 19 |
| 7 | 12 |

Example 9

$A_1$ Receptor Inhibition

Method

Competition binding experiments have been performed incubating membranes from CHO-K1 cells stably transfected with the human adenosine A1 receptor (cat. ES-010-M400UA, Perkin Elmer, Boston, Mass., USA) (5-10 μg of protein/sample) with a single concentration of [3H]DPCPX (1.7 nmol/l) (Perkin Elmer), in the presence of various concentrations (ranging from $10^{-5}$ to $10^{-10}$ M) of cold DPCPX, ST4206 and ST4208 in 96-well filter plates (MultiScreen system, cat #MAFBN0B10, Millipore, Billerica, Mass., USA) for 60 min at 25° C. in a total volume of 200 μL/well of 25 mmol/l Hepes, 5 mmol/L $MgCl_2$, 1 mmol/l $CaCl_2$, 100 mmol/L NaCl, pH 7.4 (all from Sigma-Aldrich). Non-specific binding has been determined in the presence of 250 μmol/l of cold DPCPX (8-cyclopentyl-1,3-dipropylxanthine, Sigma-Aldrich). At the end of incubation, bound and free radioligands have been separated by filtering the 96-well filter plates using a Millipore filtration apparatus (MultiscreenHTS vacuum manifold). Filter plates have been washed several times with ice-cold buffer (50 mmol/l Tris-HCl, pH 7.4) and filter-bound radioactivity measured using a MicroBeta counter (PerkinElmer) after addition of 30 μL/well of OptiPhase SuperMix scintillation cocktail (PerkinElmer).

Data have been analyzed using nonlinear regression with GraphPad PRISM commercial software. Data will be expressed as test compound concentration causing a half maximal inhibition of control values ($IC_{50}$). Inhibitory binding constant (Ki) values will be calculated from $IC_{50}$ values, according to the Cheng and Prusoff equation $K_i=IC_{50}/(1+[C]/K_d)$, where [C] is the concentration of the radioligand and $K_d$ its dissociation constant.

Results

Tested compounds bound A1 adenosine receptors with the Ki values reported in Table 2.

TABLE 2

| Examples | $A_1$ Ki nM |
|---|---|
| 1 | 51 |
| 2 | 27 |
| 5 | 120 |
| 6 | 216 |
| 7 | 197 |

Example 10 cAMP Inhibition

The compounds of the present invention were tested to assess their capacity to inhibit cAMP accumulation induced by the $A_{2A}$ agonist 5'-N-ethylcarboxamidoadenosine (NECA).

Methods cAMP quantitative determination was performed with an enzyme immunoassay system (cat. RPN2255, Amersham Biosciences) according to manufacturer's instructions. HEK 293 cells, stably expressing the human adenosine $A_{2a}$ receptor gene (PerkinElmer, Boston, Mass., USA, cat. RBHA2AC), were grown in Falcon flasks in DMEM (Cambrex, Verviers, Belgium) supplemented with 10% FBS (Cambrex), 1 mmol/l sodium pyruvate (Sigma-Aldrich, St. Louis, Mo., USA), and 0.4 mg/ml G418 (Sigma-Aldrich) at 37° C. in a 5% $CO_2$ atmosphere. Cells were plated on 96-well dishes at a concentration of $10^3$ cells/well 48 hours before test compound exposure. Before cell stimulation with the compounds, cells were treated for 10 min at 37° C. with 0.5 mmol/l of the phosphodiesterase inhibitor Ro 20-1724 (Sigma-Aldrich) and with 2 U/ml of adenosine deaminase (ADA, Sigma-Aldrich). Medium was then changed with fresh medium containing scalar concentrations of test compounds ($10^{-10}$-$10^{-4}$ mol/l) at 37° C. and, after 10 min, 100 nmol/l NECA was added. cAMP was extracted 20 min after and quantified.

Data were analyzed by nonlinear regression analysis with GraphPad PRISM commercial software. Test compound concentrations causing a half maximal inhibition of control values ($IC_{50}$ calculated by GraphPad Prism software) was reported (mean±SEM of four independent experiments).

Results

All compounds resulted efficacious at inhibiting agonist-induced cAMP accumulation (table 3) and behaved as expected for $A_{2a}$ receptor antagonists.

TABLE 3

| Examples | cAMP $IC_{50}$ µM |
|---|---|
| 1 | 2.12 |
| 2 | 0.45 |
| 3 | 0.26 |
| 4 | 0.42 |
| 5 | 2.32 |
| 6 | 2.92 |
| 7 | 0.99 |

Example 11

In order to evaluate the selectivity profile of the compounds of the present invention, three of them (ST3829, ST3932 and ST4023) were also characterized for their affinity toward a battery of 51 different receptors. The majority of the 51 assays were human recombinant receptors of the following types: adenosine, adrenergic, cannabinoid, dopamine, GABA, histamine, melatonin, muscarinic, prostanoid and serotonin receptors belonging to non peptide receptors family; angiotensin-II, bradychinin, chemokines, cholecistokinin, endothelin, galanin, melacortin, neurokinin, neuropeptide Y, neurotensin, opioid and opioid like, somatostatin, vasoactive intestinal peptide and vasopressin receptors belonging to peptide receptors family; $Ca^{2+}$ channel, $K^+$ channel and $Na^+$ channel belonging to the ion channel family and dopamine, norepinephrine and serotonin belonging to the amine transporters receptors family." These three compounds were tested at a concentration of 10 µM. Interestingly, none of them demonstrated any substantial affinity toward any of the above-mentioned receptors.

Example 12

Haloperidol-Induced Catalepsy Mice Model

ST3829, ST3932 and ST4023 were tested to assess their capacity to antagonize haloperidol-induced catalepsy in mice.

Methods

Haloperidol (2 mg/kg) was injected i.p. to CD1 mice 2.5 h before oral administration of ST3932 or ST4206. The latter were administered at doses of 10, 20 or 40 mg/kg.

Then, each CD1 mouse was gently placed by its forepaws on a wire at a height of 4.5 cm. Catalepsy was measured as the time (expressed in seconds) necessary for the animal to step down with at least one forepaw, with an end point of 60 seconds, time after which the mouse was gently removed from the wire. Then, catalepsy was scored every 60 min for seven h.

Data Evaluation

All data were expressed both as individual and mean values, plus or minus standard error (Mean±SEM) of catalepsy time in seconds. Statistical analysis was performed using sigma stat program. After calculation of AUC throughout 7 hours, the one-way ANOVA followed by Dunnett's test were used. Basal time was not considered statistically because this time-point was only used to check that catalepsy was successfully induced in all animals.

Results

Figure 1:
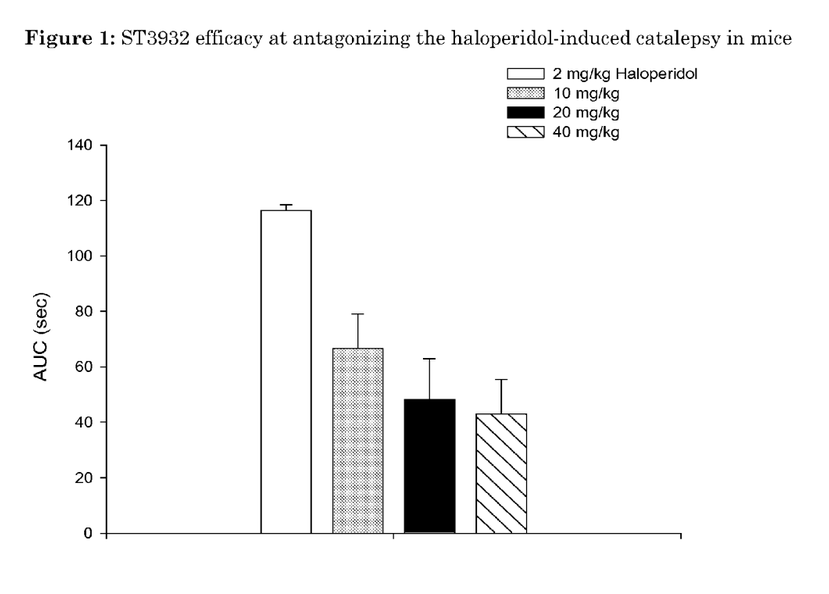
FIG. 1: it shows the efficacy of ST3932 at antagonizing the haloperidol-induced catalepsy in mice.
Figure 2:
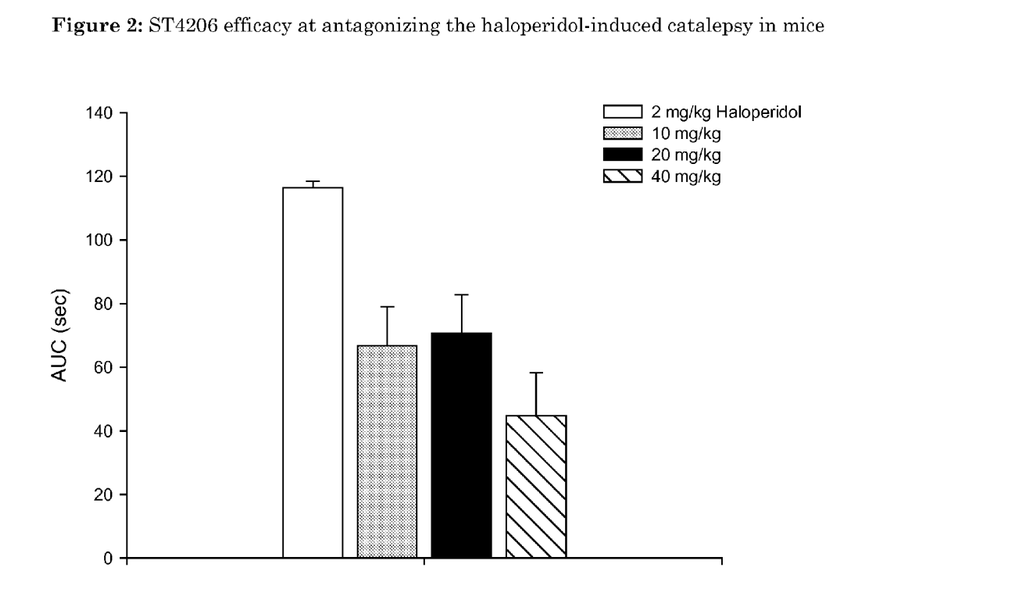
FIG. 2: it shows the efficacy of ST4206 at increasing the number of contralateral rotation of 6-OHDA lesioned rats.
Figure 3:
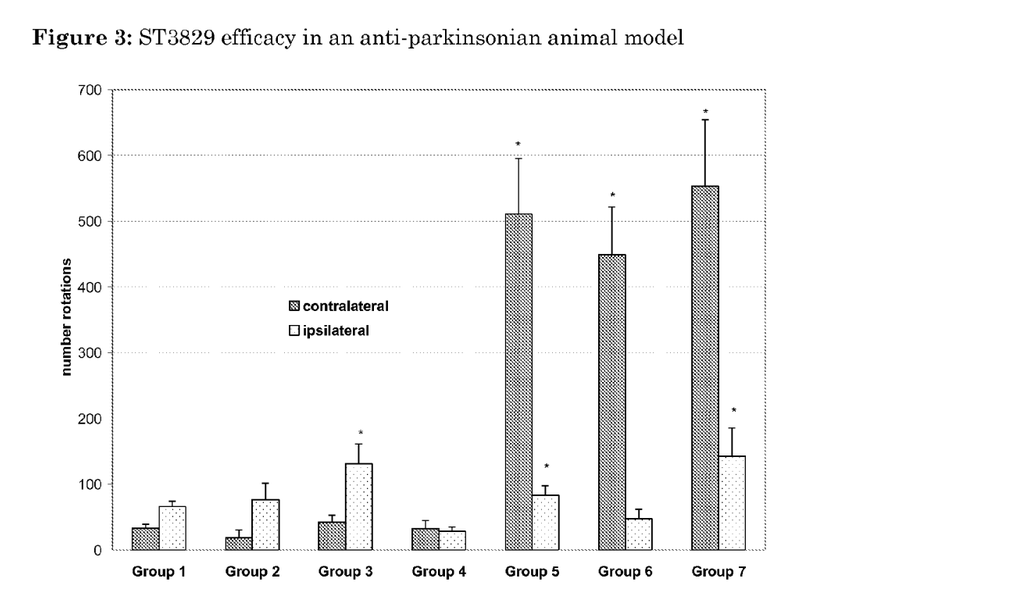
FIG. 3: it shows the efficacy of ST3829 at increasing the number of contralateral rotation of 6-OHDA lesioned rats.
Figure 4:
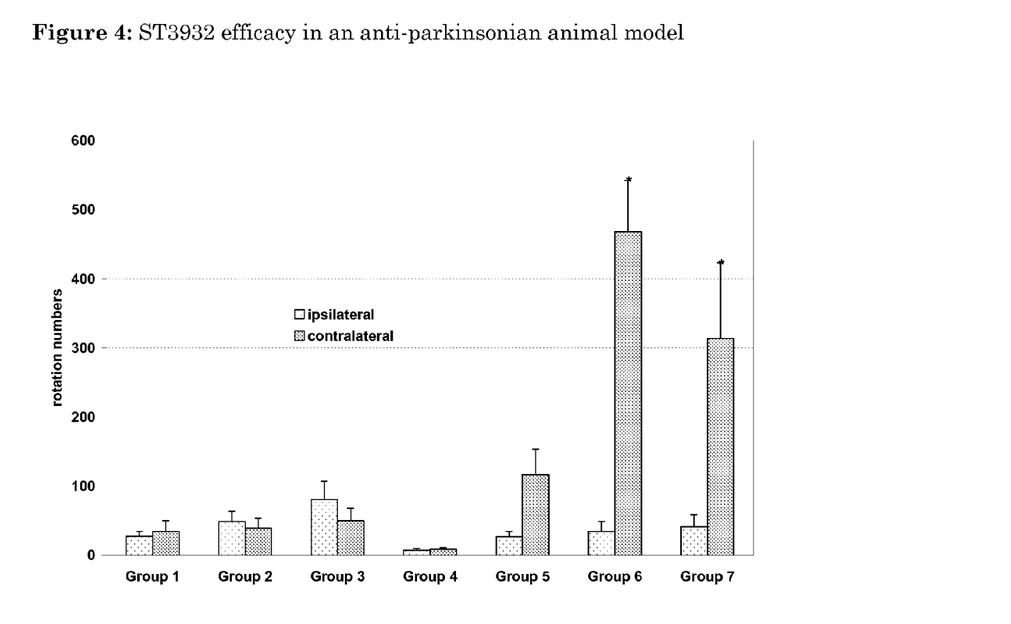
FIG. 4: it shows the efficacy of ST3932 at increasing the number of contralateral rotation of 6-OHDA lesioned rats.
Figure 5:
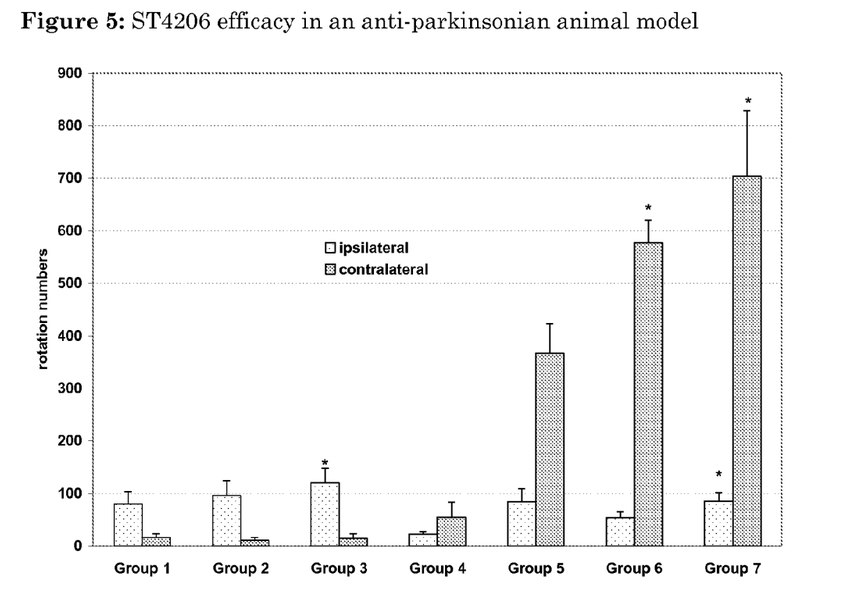
FIG. 5: it shows the efficacy of ST4206 at increasing the number of contralateral rotation of 6-OHDA lesioned rats.

Both ST3932 and ST4206 significantly antagonized haloperidol-induced catalepsy in a dose-dependent manner (FIGS. 1 and 2).

Example 13

Enhancement of L-DOPA Antiparkinsonian Activity

Rats (Sprague Dawley) under chloral hydrate (400 mg/kg) anaesthesia were placed in a Kopf stereotaxic apparatus. Through a stainless steel cannula, 6-OHDA was injected at a rate of 1 µl/min into the left medial forebrain bundle at coordinates A=−2.2, L=+1.5 and V=−7.8, according to the Pellegrino atlas. All rats, including shams, were treated with desipramine (10 mg/kg) 10 min before anaesthesia to prevent damage to noradrenergic neurons.

Two weeks after the 6-OHDA injection, all animals were tested for their contra lateral rotation capacity in response to 30 mg/kg i.p. benserazide followed by 50 mg/kg i.p. of L-Dopa 30 min later. Rats not showing at least 200 contra lateral rotations within the 3 h testing period were eliminated from the study. One week after this test, selected animals were randomized to be enrolled in three studies. Each study involved seven groups of eight animals.

Tested compounds (ST3829, ST3932 and ST4206) were dissolved in a solution containing 10% sucrose and 0.3% Tween 80 in sterile water in order to obtain three different dosage forms (i.e., 10, 20 and 40 mg/kg).

| Group 1 | Tested compound 10 mg/kg |
|---|---|
| Group 2 | Tested compound 20 mg/kg |
| Group 3 | Tested compound 40 mg/kg |
| Group 4 | 6 mg benserazide + 3 mg L-DOPA |
| Group 5 | Tested compound 10 mg/kg and 6 mg benserazide + 3 mg L-DOPA |
| Group 6 | Tested compound 20 mg/kg and 6 mg benserazide + 3 mg L-DOPA |
| Group 7 | Tested compound 40 mg/kg and 6 mg benserazide + 3 mg L-DOPA |

In groups 5, 6 and 7 benserazide was administered first, followed by the tested compound 25 min after and finally by L-DOPA 5 min later.

Results

In the 6-OHDA rat model of Parkinson's disease, adenosine A2a receptor antagonists increase turning behaviour induced by L-Dopa showing antiparkinsonian effects. In this study it was shown that ST3932 and ST4206, administered to rats with a threshold dose of L-Dopa, increased the contralateral turning behaviour induced by L-Dopa displaying a marked antiparkinsonian activity.

The invention claimed is:

1. A process for synthesizing a compound of the formula

Formula I or an optically active form, or a pharmaceutically acceptable salt thereof, wherein

$R^1$ is $C_1$-$C_6$ linear or branched alkyl;
$R^2$ is a group of formula:
$R^9$—$(CHR^8)_p$—$(CR^6R^7)_m$—$(CR^4R^5)_n$—;
$R^4$ and $R^5$ are H;
$R^6$ and $R^8$ are at any occurrence independently H or =O with the meaning of carbonyl; with at least one of $R^6$ and $R^8$ being =O with the meaning of carbonyl;
$R^7$ and $R^9$ are at any occurrence independently H or are absent in case the corresponding carbon atom bearing said $R^6$ or $R^8$ group is involved in a carbonyl bond;
m and p are independently an integer comprised between 0 and 2;
n is 1 or 2;
m+n+p≥4;
$R^3$ is $NH_2$ or $NHR^{10}$;
$R^{10}$ is linear or branched $C_1$-$C_6$ alkyl; linear or branched $C_1$-$C_6$ hydroxyalkyl; linear or branched $(C_1$-$C_3)$alkoxy$(C_1$-$C_6)$alkyl; amino$(C_1$-$C_6)$alkyl, where the amino group is optionally substituted with one or two linear or branched $C_1$-$C_3$ alkyl groups; $C_6$-$C_{14}$ aryl; or $C_6$-$C_{14}$ aryl$(C_1$-$C_6)$alkyl, wherein said $C_6$-$C_{14}$ aryl group is optionally substituted by one or more substituents, which are the same or different, selected from the group consisting of halogen; hydroxyl; linear or branched, saturated or unsaturated $C_1$-$C_6$ alkoxy; and amino, where the amino group is optionally substituted with one or two linear or branched $C_1$-$C_6$ alkyl groups comprising the reaction between a compound of formula II Formula II wherein
$R^1$ is $C_1$-$C_6$ linear or branched alkyl;
$R^{11}$ is N $(R^{13})_2$;
$R^{13}$ is benzyl, p-(MeO)-benzyl, p-(Cl)-benzyl or p-(Br)-benzyl;
$R^{12}$ is Cl;
and a compound of formula IV Formula IV, wherein
X is Cl or Br;
$R^{6b}$ and $R^{6c}$ are at any occurrence independently both H or when taken together with the carbon atom to which they are attached to form a 1,3-dioxane group optionally substituted by two or more methyl groups with at least one of the occurrence being a 1,3-dioxane group optionally substituted by two or more methyl groups;
q is an integer comprised between 0 and 3;
r and s are independently an integer comprised between 1 and 3; with q+r+s≥4;
in the presence of a Fe(acac)$_3$ in an aprotic solvent at a temperature ranging from 0° C. to room temperature.

2. Process according to claim 1 wherein the aprotic solvent is THF or NMP.

* * * * *